United States Patent
Young et al.

(10) Patent No.: US 7,273,480 B2
(45) Date of Patent: *Sep. 25, 2007

(54) COMPOSITE MATERIAL BRAIDED INSULATOR

(75) Inventors: Kimbolt Young, Newtonville, MA (US); Gerald M. Hubbs, Bloomingdale, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/637,471

(22) Filed: Dec. 11, 2006

(65) Prior Publication Data

US 2007/0088350 A1    Apr. 19, 2007

Related U.S. Application Data

(63) Continuation of application No. 10/929,298, filed on Aug. 30, 2004, now Pat. No. 7,166,104.

(51) Int. Cl.
*A61B 18/14*    (2006.01)

(52) U.S. Cl. .............................. 606/41; 606/48; 606/50

(58) Field of Classification Search .................. 606/41, 606/48, 50
See application file for complete search history.

(56) References Cited

U.S. PATENT DOCUMENTS

| | | | | |
|---|---|---|---|---|
| 5,403,311 | A * | 4/1995 | Abele et al. ................... | 606/49 |
| 5,531,677 | A * | 7/1996 | Lundquist et al. ............. | 604/22 |
| 6,017,338 | A * | 1/2000 | Brucker et al. ................ | 606/41 |
| 6,235,021 | B1 * | 5/2001 | Sieben ......................... | 606/41 |
| 6,572,613 | B1 * | 6/2003 | Ellman et al. ................. | 606/45 |
| 6,602,242 | B1 * | 8/2003 | Fung et al. .................... | 606/41 |
| 6,723,094 | B1 * | 4/2004 | Desinger ...................... | 606/50 |
| 6,740,084 | B2 * | 5/2004 | Ryan ............................ | 606/41 |
| 7,166,104 | B2 * | 1/2007 | Young et al. .................. | 606/41 |

* cited by examiner

*Primary Examiner*—Lee S. Cohen
(74) *Attorney, Agent, or Firm*—Kay Kaplun & Marcin, LLP.

(57) ABSTRACT

A tissue penetrating probe includes a distal tissue piercing end; a first electrode; a second electrode; and a dielectric element. A proximal end of the dielectric element is bonded to a distal end of the first electrode and a distal end of the dielectric element is bonded to a proximal end of the second electrode. The dielectric element is formed of a composite material including a fiber braid within a polymeric material.

14 Claims, 2 Drawing Sheets

COMPOSITE MATERIAL BRAIDED INSULATOR

The present application is a Continuation application of U.S. patent application Ser. No. 10/929,298 filed Aug. 30, 2004, now U.S. Pat. No. 7,166,104, the entire disclosure of which is expressly incorporated herein by reference.

BACKGROUND OF THE INVENTION

Ablation is often the recommended treatment for fibroids, tumors or other abnormal tissue masses. Local ablation of the diseased tissue may be carried out by inserting a therapeutic device into the tissue and carrying out therapeutic activity designed to treat the diseased cells. For example, tissue may be ablated by placing one or more electrodes into the affected tissue and discharging electric current therefrom. Various types of probes may be used to reach the target tissue and deliver electric energy thereto. One type of probe commonly used is the needle probe.

Needle probes are often used to carry out the RF ablation treatments because they are able to pierce the surfaces of many tissue masses and to penetrate to an optimal location within these masses for treatment. The needle probes may be either monopolar with a single polarity electrode on the probe and a second external electrode (e.g., a grounding pad) used to complete the circuit or bipolar with electrodes of opposite polarity mounted on the probe separated from one another by an insulator.

The size of the RF ablation probes is generally kept to a minimum to reduce trauma and to facilitate accurate placement of the probe so that target tissue may be ablated with minimal damage to surrounding healthy tissue. The construction of small diameter ablation probes is difficult because, in use, these probes are subjected to compressive loads. In particular, it is difficult to construct small insulating elements to separate electrodes (e.g., in a bipolar device) which are able to withstand the compressive loads to which they will be subjected.

SUMMARY OF THE INVENTION

The present invention relates to a tissue penetrating probe includes a distal tissue piercing end; a first electrode; a second electrode; and a dielectric element. A proximal end of the dielectric element is bonded to a distal end of the first electrode and a distal end of the dielectric element is bonded to a proximal end of the second electrode. The dielectric element is formed of a composite material including a fiber braid within a polymeric material.

DETAILED DESCRIPTION

Figure 1:
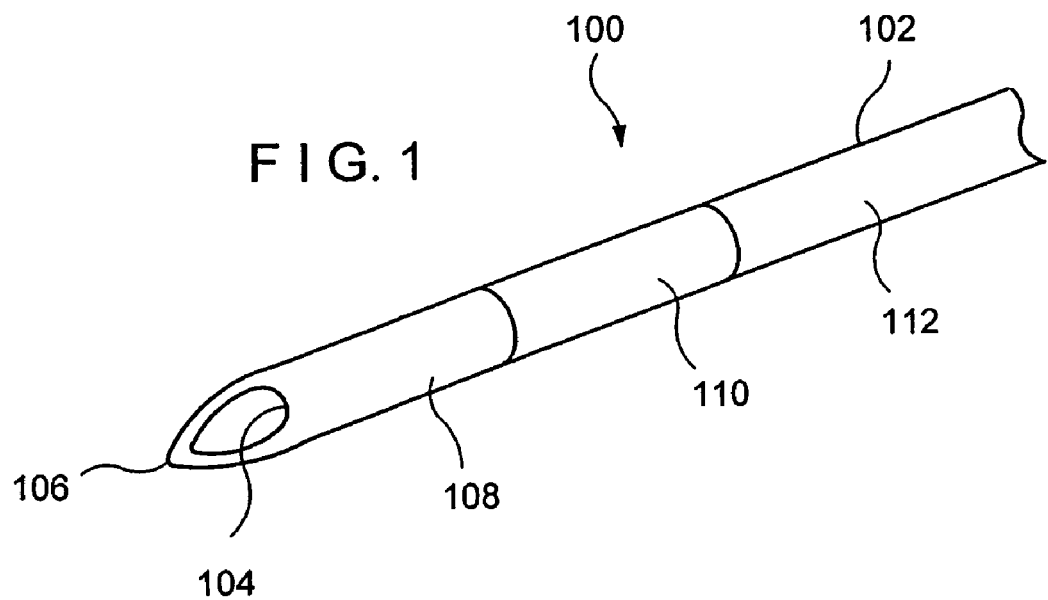
FIG. 1 is a perspective depiction of the RF ablation probe according to an embodiment of the present invention.

The present invention may be further understood with reference to the following description and the appended drawings, wherein like elements are referred to with the same reference numerals. The present invention is related to medical devices for ablating abnormal tissues. More specifically, the invention is related to devices for ablating tissues such as tumors, fibroids and other abnormal growths using RF energy. The invention is also related to devices adapted to treat tissue within hollow organs or body lumens of the patient.

A variety of ablation techniques have been employed to treat various tumors, fibroids and other abnormal tissue growths. Heat ablation, RF ablation and chemical ablation are a few of the techniques available to necrose abnormal tissues, which may then be surgically removed. These techniques are especially well suited for growths within hollow organs, such as the GI tract, the uterus, etc. In some cases, an endoscope or similar instrument may be necessary to reach the target tissue. In those cases the ablation device is often sized to fit within a working lumen of the endoscope.

As discussed above, size and durability constraints for bipolar RF probes have posed several challenges. For bipolar probes which are needle-like or otherwise include a hollow tubular member, wires or other conductors are often threaded through a lumen of the probe to connect each of the electrodes to a power source. In particular, the most distal electrode may require that a conductor pass through the more proximal electrode and an insulator separating the electrodes to connect with the power supply. Thus these insulators have often been formed as hollow tubular elements.

Ablation probes and, in particular, insulators of bipolar RF ablation probes must also be designed to support mechanical loads. For example, an RF ablation probe may be used as a needle to penetrate target tissue and may need to pass through other tissue in order to reach the target tissue. In some cases, the probe must be pushed through the working lumen of an endoscope or similar instrument before reaching the target tissue. Accordingly, the probe and its components are preferably formed with sufficient column strength to resist operative compressive and bending loads without buckling or other undesired deformation. Once such a bipolar probe has been positioned within or abutting target tissue, a high frequency alternating current may be applied to the electrodes so that current flows from one electrode to the other through the target tissue to heat and, if enough energy is applied, to necrose the tissue.

FIG. 1 shows an exemplary embodiment of a bipolar ablation probe according to the present invention. The probe 100 comprises a needle-like elongated body 102 which terminates in a sharp distal end 106. The sharp end 106 may be used to facilitate penetration of the probe 100 through tissue to reach desired locations within the body. Various configurations of the sharp distal end 106 may be used, depending on the desired use of the ablation probe 100 or a more blunt configurations may be used for applications which do not require penetration of puncture resistant tissues. A lumen 104 extends through the elongated body 102 to provide a passage through the probe 100. One skilled in the art would understand that the probe 100 may also include any of other known types of ablation electrodes including, for example, electrodes formed as a deployable array of tines which, during insertion and removal from the body, are received within a central lumen of the probe 100. In addition, the central lumen of the probe 100 may be used to receive guidewires and other medical devices which may be deployed or retracted therethrough to the target tissue. FIG. 1 depicts only the distal end of the probe 100, which is designed to contact the target tissue to deliver RF energy thereto. As would be understood by those skilled in the art, the probe 100 may also include a handle portion, electric contacts, an insulated body and electric controls.

A distal electrode 108 and a proximal electrode 112 form the energy delivering portion of the ablation probe 100. Each of the proximal and distal electrodes 108, 112, respectively, is formed of an electrically conductive material which is also biocompatible and which possesses sufficient mechanical strength to resist buckling and deformation in normal use. For example, stainless steel or other metals may be used. As the ablation probe 100 is typically very thin, metal electrodes are preferred to provide the required structural strength. As the electrodes 108, 112 are of different polarities, it is necessary to separate them with an insulator such as a dielectric element 110 to prevent short circuits and to cause the current to flow from one electrode to the other through the target tissue. As would be understood by those skilled in the art, the length of the dielectric element 110 may be selected to obtain a desired performance of the probe 100.

As indicated above, the ablation probe 100 is preferably of low profile and of very small gauge, to minimize the trauma. As described above, in addition to being a structural member of the probe 100, the dielectric element 110 must also be biocompatible and be bondable or otherwise attachable to the metallic cannulas that form the electrodes 108, 112. In the exemplary embodiment shown in FIG. 3, the dielectric element 110 is formed as a substantially tubular shell with a wall thickness t of between about 0.004 and about 0.007 inches. The inner diameter ID of the dielectric element 110 according to this embodiment is approximately 0.05 inches and the outer diameter OD is approximately 0.06 inches.

According to an embodiment of the present invention, the tubular dielectric element 110 comprises a polymeric filler material 120 containing an encapsulated fiber braid 122. This construction results in a composite material of dielectric strength sufficient to insulate the electrodes 108, 112 from one another while providing column strength sufficient to resist buckling or bending under operative loads to which the probe 100 is to be subjected. For example, when subjected to compressive loads of 3.5 to 4 pounds, the metal cannulas used to form the electrodes of a dielectric element constructed as described failed while the dielectric portions of the element retained their structural integrity. In one exemplary embodiment, the filler material is a polyamide material with a braid of Vectran fiber (Celanese Acetate LLC, Charlotte, N.C.). The combination of polyamide and the Vectran fiber braid results in a composite material having the desired mechanical and insulation properties for use in the contemplated applications. Alternatively, the fiber braid 122 may comprise braided fibers of metal or other electrically conductive material so long as these fibers are fully encapsulated in a dielectric material. One skilled in the art would understand that the polymeric filler material 120, may be replaced by any other non-conductive material suitable to insulate the electrodes including, for example, ceramics and rubbers.

As described above, according to the present embodiment, the column strength of the resulting composite material is comparable to that of the metal cannulas conventionally used to form the proximal and distal electrodes 108, 112. In an exemplary embodiment, the metallic cannulas that form the electrodes 108, 112 have an inner diameter between approximately 0.03 and 0.05 inches and an outer diameter of between 0.05 and 0.07 inches and, more preferably, has an inner diameter of approximately 0.043 inches and an outer diameter of approximately 0.060 inches. The composite material is thus well suited for use in a medical device such as the RF ablation probe 100, so that the elongated body 102 exhibits relatively uniform mechanical properties along its length. The user thus may push the probe 100 through the working lumen of the endoscope or through the biological tissue without the dielectric element 110 buckling or bending under the operative axial load before the failure of the metal components of the probe 100.

Figure 2:
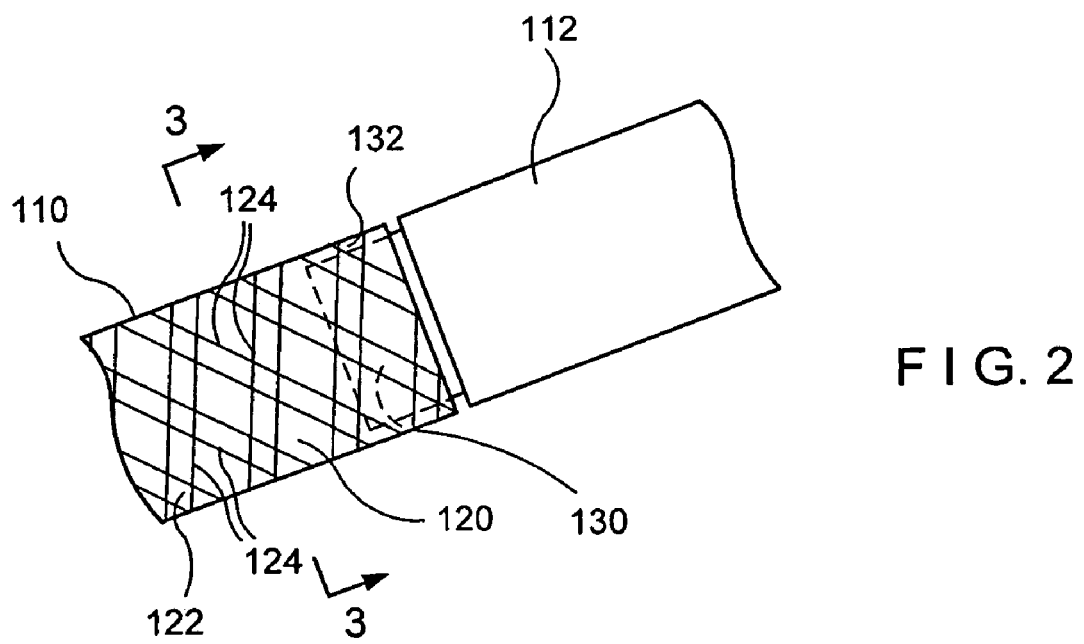
FIG. 2 is a detail view of the structural insulator bonded to the metal conductor of the RF ablation probe where the insulator overlaps the conductor_shown in FIG. 1.
Figure 3:
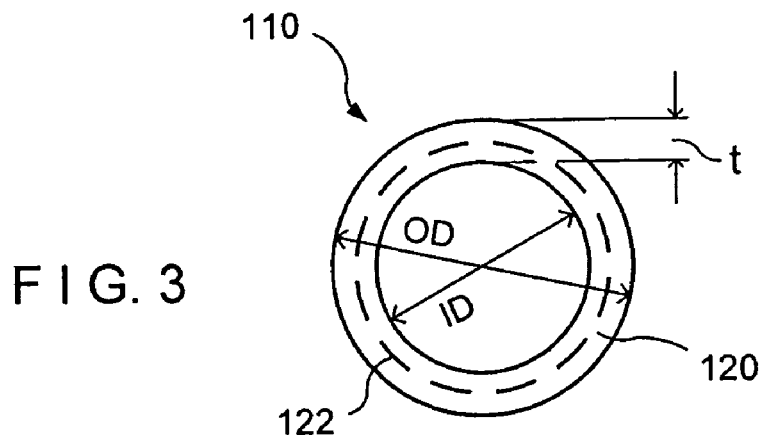
FIG. 3 is a cross sectional view along line III-III of the structural insulator shown in FIG. 2.

As shown in FIGS. 2 and 3, the fiber braid 122 may be formed of a plurality of bands of fibers 124 overlapping one another in a cris-cross pattern. As would be understood by those skilled in the art, the shape of the pattern and the fiber count per unit length may be modified to obtain a desired column strength of the dielectric element 110 or to facilitate manufacture of the component. The cost and expected use of the resulting probe 100 may also be considerations in determining the configuration of the fiber braid 122. According to the exemplary embodiment of the invention shown in FIGS. 1-4, the composite material results in the dielectric element 110 which is substantially rigid. However, for certain applications, it may be desirable to modify the polymeric material 120 and/or the fiber braid 122 such that the resulting composite material will retain a degree of flexibility. For example, the pattern and type of fiber bands 124 may be modified to achieve selected mechanical properties. The material may thus retain a high column strength to resist compression, but may be bendable along its longitudinal axis. In a preferred embodiment, the fiber braid 122 is formed with a plurality of bands of fibers 124 arranged in a cris-cross pattern at approximately 60 PIC (crisscrosses per inch).

Figure 4:
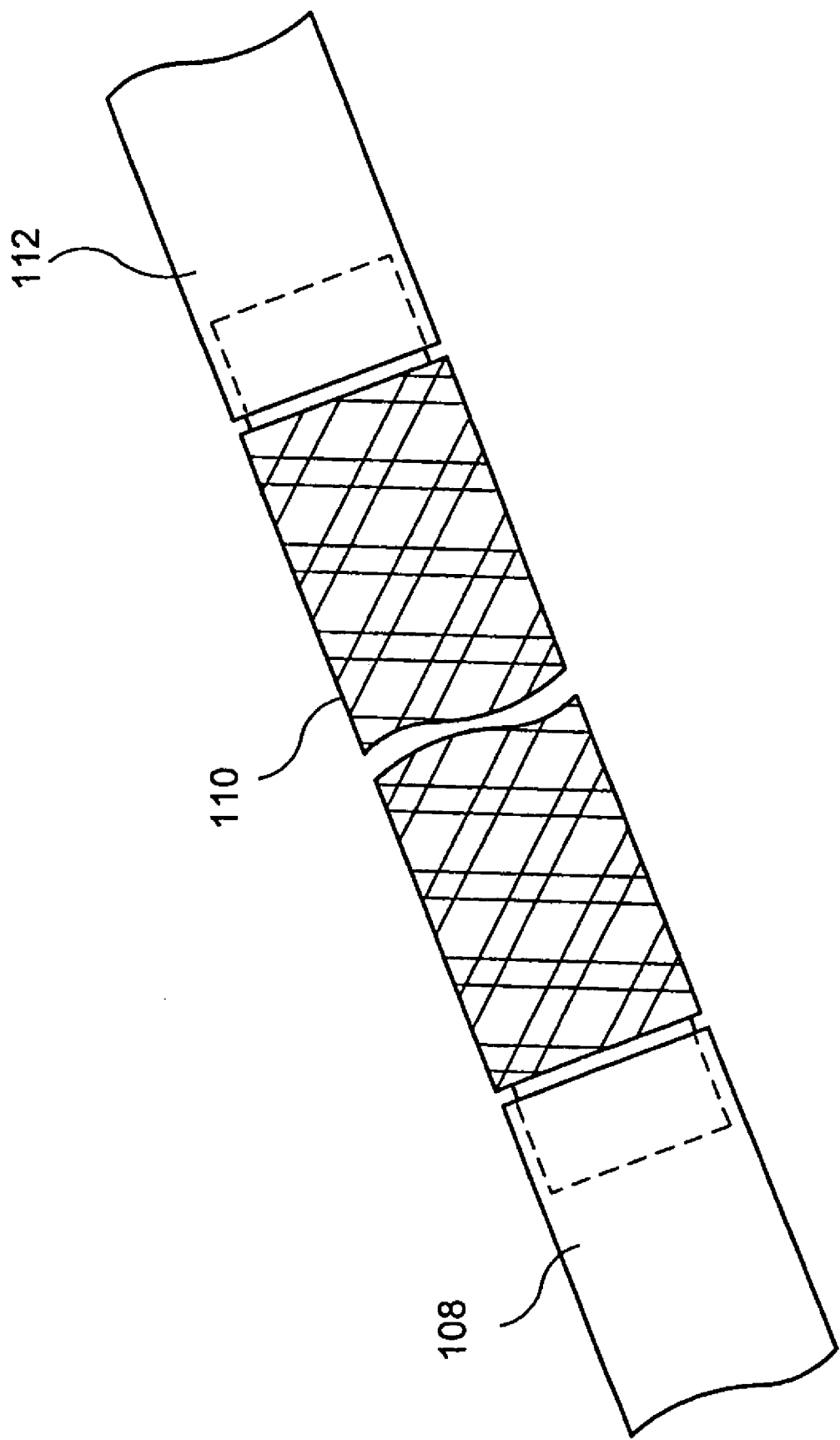
FIG. 4 is a detail view of the structural insulator bonded to the metal conductor of the RF ablation probe where the conductor overlaps the insulator shown in FIG. 1.

An additional feature of the dielectric element 110 is that it can be securely attached to the distal and proximal electrodes 108, 110. As shown in FIG. 2, an overlapping joint is formed between reduced diameter portions 130 of the electrodes 112, 108 and overlap portions 132 of the dielectric element 110. The inner, reduced diameter portions of the overlapping joint are preferably formed from the metal electrodes 108, 112 rather than from the composite dielectric element 110, since the metal of which the electrodes 108, 112 are formed will generally exhibit mechanical properties at the reduced diameter superior to those of the composite material. However, as shown in FIG. 4, depending on the mechanical properties of the composite material forming the dielectric element 110, an opposite configuration where the composite material forms the reduced diameter portion may also be used.

Multiple techniques may be used to bond the composite material of the dielectric element 110 to the metallic electrodes 108, 112. For example, an adhesive may be placed at the interface of the reduced diameter sections 130 and the overlap portions 132, to securely bind the dielectric element 110 to the electrodes 108, 112. Various known biocompatible adhesives such as Loctite (Henkel Loctite Corp.-Industrial, Rocky Hill, Conn.) may be used for this purpose. If the composite material forming the dielectric element 110 comprises a polyamide base polymer with Vectran fiber, Ultra-Violet (UV) bonding methods may also be used. The use of polyamide with encapsulated Vectran together with the thin nature of the walls of dielectric element 110 produces a translucent dielectric element 110, through which UV light may reach the interface between the two components. UV curing of the adhesive may thus be carried out to join the components as would be understood by those skilled in the art.

The present invention has been described with reference to specific embodiments, and more specifically to the distal structural dielectric element used to separate the electrodes of a bipolar ablation probe. However, other embodiments may be devised that are applicable to other procedures and devices, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A tissue penetrating probe, comprising
a distal tissue piercing end;
a first electrode;
a second electrode; and
a dielectric element, a proximal end of the dielectric element being bonded to a distal end of the first electrode and a distal end of the dielectric element being bonded to a proximal end of the second electrode, the dielectric element being formed of a composite material including a fiber braid within a polymeric material.

2. The ablation probe according to claim 1, further comprising a first electric conductor extending proximally from a distal end coupled to the second electrode, through the dielectric element, through the first electrode to a source of ablation energy.

3. The ablation probe according to claim 2, further comprising a second electric conductor extending proximally from a distal end coupled to the first electrode to the source of ablation energy.

4. The ablation probe according to claim 1, wherein the probe is formed as a substantially tubular elongated member with each of the first and second electrodes and the dielectric element forming substantially cylindrical portions of the substantially tubular member.

5. The ablation probe according to claim 4, wherein the first and second electrodes and the dielectric element are substantially aligned along a longitudinal axis of the elongated member.

6. The ablation probe according to claim 1, wherein the polymeric material is extruded polyamide.

7. The ablation probe according to claim 1, wherein each of the first and second electrodes is formed of a metal cannula.

8. The ablation probe according to claim 1, wherein a length of the dielectric element is selected to optimize a distance between the first and second electrodes.

9. The ablation probe according to claim 1, wherein the dielectric element is bonded to each of the first and second electrodes using one of an adhesive and Ultra Violet bonding.

10. The ablation probe according to claim 1, wherein the dielectric element includes reduced diameter proximal and distal portions which are received within overlapping portions of the first and second electrodes, respectively.

11. The ablation probe according to claim 10, wherein at least one of the first and second electrodes includes a reduced diameter portion received within an overlapping portion of the dielectric element.

12. The ablation probe according to claim 10, wherein the dielectric element includes a reduced diameter portion, the reduced diameter portion being received within an overlapping portion of at least one of the first and second electrodes.

13. The ablation probe according to claim 1, wherein the dielectric element has a thickness of between about 0.005 inches and about 0.006 inches.

14. The ablation probe according to claim 13, wherein the probe is formed as a substantially tubular elongated member and wherein the tubular member has an inner diameter of about 0.05 inches and an outer diameter of about 0.06 inches.

* * * * *